United States Patent [19]

Aubard et al.

[11] Patent Number: 4,994,617

[45] Date of Patent: Feb. 19, 1991

[54] AMINOALCOHOLS, THEIR PREPARATION PROCESS AND THEIR APPLICATIONS, PARTICULARLY IN THERAPEUTICS

[75] Inventors: Gilbert Aubard, Palaiseau; Jacques Bure, Neuilly sur Seine; Alain P. Calvet, Versailles; Claude Gouret; Agnes G. Grouhel, both of Meudon; Jean-Louis Junien, Paris, all of France

[73] Assignee: Jouveinal S.A., Paris, France

[21] Appl. No.: 456,743

[22] Filed: Dec. 26, 1989

Related U.S. Application Data

[63] Continuation of Ser. No. 3,276, Jan. 14, 1987, abandoned.

[30] Foreign Application Priority Data

Jan. 30, 1986 [FR] France ................. 86 01295

[51] Int. Cl.$^5$ ............... A61K 31/135; C07C 215/00
[52] U.S. Cl. ............................................ 564/355
[58] Field of Search ................... 564/355; 514/653

[56] References Cited

U.S. PATENT DOCUMENTS

| | | | |
|---|---|---|---|
| 3,132,179 | 5/1964 | Clarke | 564/355 |
| 3,193,581 | 7/1965 | Shinohara et al. | 564/360 X |
| 3,573,304 | 3/1971 | Eberle et al. | 564/355 X |
| 3,706,764 | 12/1972 | Nakanishi et al. | 564/355 X |
| 3,804,899 | 4/1974 | Ebnother et al. | 564/355 X |
| 3,896,166 | 7/1975 | Kaiser et al. | 564/374 X |
| 4,058,642 | 11/1977 | Renth et al. | 564/356 X |
| 4,075,241 | 2/1978 | Bellasio et al. | 564/355 X |
| 4,536,601 | 8/1985 | Tukamoto et al. | 564/373 X |

FOREIGN PATENT DOCUMENTS 1434826  5/1976  United Kingdom ............... 564/355

Primary Examiner—Robert V. Hines
Attorney, Agent, or Firm—Cushman, Darby & Cushman

[57] ABSTRACT

Aminoalcohols of formula:

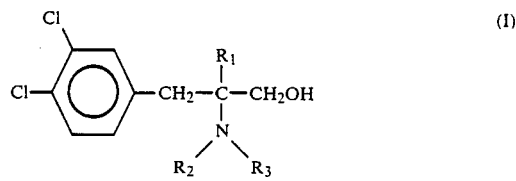

(I)

in which $R_1$ is alkyl, $R_2$ H or alkyl, $R_3$ in particularly H, alkyl, phenylakyl, alkanoyl, phenylalkanoyl, in which N, $R_2$ and $R_3$ together form a heterocycle saturated with 5 to 7 chain links.

Analgesic medicaments.

12 Claims, No Drawings

AMINOALCOHOLS, THEIR PREPARATION PROCESS AND THEIR APPLICATIONS, PARTICULARLY IN THERAPEUTICS

This is a continuation of application Ser. No. 07/003,276, filed Jan. 14, 1987, and now abandoned.

One present invention relates to novel aminoalcohols derived from 2-(3,4-dichlorobenzyl)-2-aminoethanol, their preparation process and their applications, particularly in therapeutics.

The invention relates to novel aminoalcohols of formula

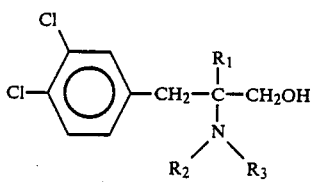

in which $R_1$ is lower alkyl and $R_2$ is H or lower alkyl, $R_3$ is H, lower alkyl, lower alkenyl, lower phenylalkyl or lower cycloalkylalkyl with 3 to 6 carbon atoms in the cycle or, when $R_2$ is H, lower alkanoyl, lower phenylalkanoyl or cycloalkylcarbonyl having 3 to 6 carbon atoms in the cycle, or $R_2$ and $R_3$ form together with the nitrogen atom to which they are linked, a heterocycle saturated with 5 to 7 chain links which can have, as the second heteroatom not directly connected to the nitrogen atom, an oxygen, a sulphur or a nitrogen, the latter nitrogen heteroatom possibly carrying an alkyl substituent in $C_2$ to $C_4$, and their acid addition salts.

The lower alkanoyl and alkyl radicals are straight or branched chain and have 1 to 5 carbon atoms, the alkenyl radical preferably having 2 to 5 carbon atoms and in particular 3 carbon atoms, whilst the cycloalkyl radicals preferably have 3 to 6 carbon atoms.

Among the in particular therapeutically acceptable acids forming the addition salts with the compounds according to the invention, reference can be made in exemplified manner to mineral or organic acids, such as acetic, benzenesulphonic, camphosulphonic, citric, ethanesulphonic, fumaric, hydrobromic, hydrochloric, lactic, maleic, malic, methanesulphonic, nitric, pamoic, phosphoric, salicylic, stearic, succinic, sulphuric and tartaric acids.

The invention relates to both to the racemic and the optically active forms of the compounds of the formula (I).

The compounds according to the invention act on the central nervous system (SNC) and also have analgesic properties unexpected in aminoalcohols. Thus, the invention aims at the use of compounds (I) as analgesics and medicaments acting on the central nervous system.

Among the compounds according to the invention, preference is given to those in which $R_1$ is methyl, $R_2$ hydrogen or methyl, and $R_3$ hydrogen or methyl.

The invention is also directed at a process for the preparation of compounds of the invention comprising reducing an acid of formula

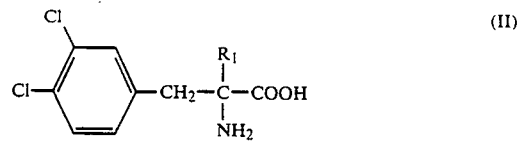

by a boron or aluminium hydride to obtain compounds (Ia), in which $R_2$ and $R_3$ are hydrogen and for obtaining compounds (Ib), in which $NR_2R_3$ form a heterocycle performing a cyclization by reacting a compound (Ia) with a reagent of formula

$$x-(CH_2)_m-R_5-(CH_2)_n-X'$$

in which X and X', which can be the same or different, are halogen, $R_5$ is a single valence bond and m and n are integers between 1 and 3, with m+n equal to or greater than 4 and equal to or less than 6, or $R_5$ is an oxygen, a sulphur or $NR_6$, $R_6$ being H or alkyl in $C_1$ to $C_4$ and m and n are integers between 1 and 3 with m+n equal to or higher than 3 and equal to or lower than 5 and for preparing compounds (Ic), in which $R_3$ is alkanoyl, phenylalkanoyl or cycloalkylcarbonyl, acylating a compound (Ia) with an acylating agent of formula $R_4$-COX, in which X is a halogen and $R_4$ is the homolog immediately below $R_3$ and for preparing compounds (Id), in which $R_2$ is H and $R_3$ is alkyl, alkenyl, phenylalkyl or cycloalkylalkyl, alkylating a compound (Ia) using an alkylating agent $R_3$-X, X being a halogen, or reducing a compound (Ic) by a boron or aluminium hydride, or reducing a compound of formula

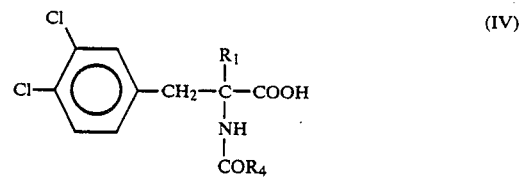

by a boron or aluminium hydride and for preparing compounds (Ie), in which $R_2$ is alkyl and $R_3$ identical to $R_2$, reacting a compound (Ia) with an aldehyde of formula $R_4$CHO in the presence of formic acid and for preparing compounds (Ie) in which $R_2$ is alkyl and $R_3$ is alkyl, alkenyl, phenylalkyl or cycloalkylalkyl, reacting a compound (Id) with an aldehyde of formula $R_4$CHO in the presence of formic acid and, for preparing the acid addition salts, reacting the compounds (I) with an acid.

The process for the preparation of the compounds according to the invention is summarized in the following table A, the dichlorobenzyl radical not being shown in the formulas of the compounds of table A.

TABLE A

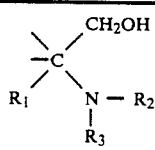

Ib

TABLE A-continued

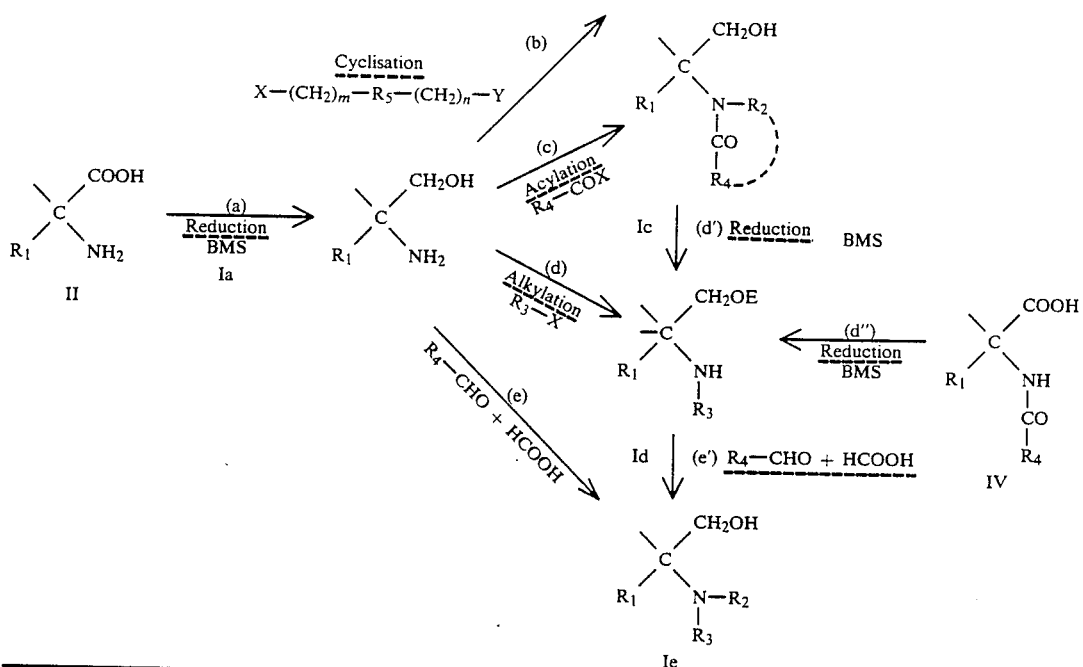

The starting products for the preparation of compounds according to the invention are optically active for racemic aminoacids of formulas (II) and (IV):

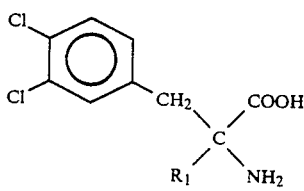

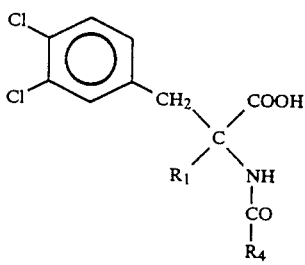

in which $R_1$ is a lower alkyl radical with the same definition as that of formula (I)a, $R_4$ is hydrogen, a lower alkyl radical, a lower phenylalkyl radical or a cycloalkyl radical, $R_4$ being the homolog immediately below $R_3$ ($R_3$=—$CH_2R_4$).

The compounds of formulas II and IV can be prepared by various processes, including that described in examples 1 and 2 of French specification 77 02360, which firstly consists of condensing the 3,4-dichlorobenzyl chloride or bromide with isocyano-esters of formula III

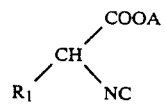

in which $R_1$ is a lower alkyl radical as defined hereinbefore and A is an alkyl radical with a low molecular mass in order to obtain, according to example 1 of said specification, racemic aminoacids of formula II.

Applied to these compounds, the process of example 2 of said specification makes it possible to obtain the products of formula IV in racemic and optically active form, as well as aminoacids of formula II in optically active forms.

As shown by table A, compounds Ia, Ib, Ic, Id and Ie in which $R_1$ is a lower alkyl radical as defined hereinbefore are in accordance with the compounds of general formula I of the invention and are prepared from compounds II and IV by the following reactions: the compounds of formula Ia are obtained by reduction of the carboxylic functions of compounds II under the action of reducing agents, such as boron or aluminium hydrides according to reaction (a), The compounds of formula Ib are obtained by cyclization reaction on the amino function of compounds Ia according to reaction (b) with the compounds of formula:

$$X-(CH_2)_m-R_5-(CH_2)_n-X'$$

in which X and X', which can be the same or different, are halogen atoms, such as iodine, bromine or chlorine, $R_5$ is a valence bond or represents an oxygen atom, sulphur or $NR_6$, $R_6$ being H or alkyl in $C_1$ to $C_4$, m and n are 1, 2 or 3, the compounds Ib obtained being characterized in that the radicals $R_2$ and $R_3$ of formula I form, with the nitrogen atom to which they are linked, a heterocycle saturated with 5 to 7 atoms which can comprise a second heteroatom formed by nitrogen, oxygen or sulphur, the compounds of formula Ic are prepared according to reaction (c) by N-acylation of compounds Ia with alkanoyl halides of formula

R<sub>4</sub>—COX in which X is a halogen atom, such as chlorine or bromine, R$_4$ is a lower alkyl radical or a lower phenylalkyl, R$_4$ being the radical immediately below R$_3$ (R$_3$=CH$_2$R$_4$), or R$_4$ is cycloalkyl, the compounds of formula Id are prepared from compounds Ia, Ic, IV by means of the following reactions:

(d) the reaction of the alkenyl halides of formula R$_3$—X, in which X is a halogen atom, such as bromine and R$_3$ an alkenyl, such as the allyl radical with the compounds of formula Ia leads to the corresponding derivatives Id, (d') consists of reducing the N-alkoyl function of the previously described compounds Ic by reducing agents identical to those of reaction (a) to obtain compounds Id, in which R$_3$ is a lower alkyl radical, a lower phenylalkyl radical or a cycloalkylalkyl radical, (d'') consists of reducing both the carboxyl and N-alkoyl functions of the previously described compound IV by the aforementioned reducing agents in order to obtain compounds Id identical to those obtained by reaction (d'), the preparation of the compounds of structure Ie is carried out on the basis of compounds Ia and Id according to the following reactions:

(e) the aminoalcohols of formula Ia by reducing dialkylation under the action of aldehydes of formula R$_4$—CHO, in which R$_4$ is hydrogen or a lower alkyl radical, and formic acid make it possible to obtain compounds of structure I, in which R$_2$ and R$_3$, which are identical, are lower alkyl radicals and in particular methyl radicals, (e') by reducing monoalkylation, as described in reaction (e), the compounds of structure Id make it possible to obtain compounds Ie, in which R$_2$ is a lower alkyl radical and in particular methyl, R$_3$ being the corresponding radicals of Id obtained by reaction (d), (d') and d'').

As has been stated, the products according to the invention are obtained by the following reactions: reductions (a), (d'), (d'') monoalkylation or dialkylation (b), (d), (e) and (e') acylation (c).

The reducing reactions consist of reducing the carbonyl groups of the carboxyl functions and/or amide functions to respectively obtain the primary alcohol and/or secondary amine functions.

These reductions make use of known methods and reagents, which are summarized in the table given in "Advanced Organic Chemistry", p 1118 (J. March, second French edition, 1977 - McGraw Hill). The reducing agents, such as boron and aluminium hydride derivatives are indicated as being effective for performing these reactions. This more particularly applies to lithium-aluminium hydride and to the borane dimethylsulphide complex (BSM hereinafter), which is the preferred reagent.

The reductions take place in non-dissociating aprotic media in solvents such as diethyl ether, diisopropyl ether, 1,2-dimethoxyethane or tetrahydrofuran (THF), which is the preferred solvent.

The BMS complex is used in stoichiometric excess compared with the products to be reduced in order to obtain a complete reaction. This excess differs as a function of the nature of the structure used and is dependent on the one hand on the number of carbonyl groups to be reduced and on the other hand on the presence in said structures of other groups or functions reacting with the BMS. Thus, as a function of the particular case, use is made of 2 to 8 mols of BMS per mol of product to be treated, whilst the preferred quantities are 2.5 to 3.5 mols of BMS per mol of compound Ic (reaction d') and 4 to 6 mols per mol of compounds II and IV (reactions a and d'').

The products undergoing the reducing reaction, namely 1 to 10 parts by weight are introduced, protected from moisture and under a nitrogen atmosphere, into 100 parts by volume of THF and more particularly 3 to 7 parts in 100 parts. The previously defined BMS quality is introduced, followed by refluxing the mixture to have a total reaction and this can take between 30 minutes and 10 hours. However, the most favourable time is 3 to 5 hours. The aminoalcohol is then released from its complex with the reducing agent by adding methanol, followed by sodium hydroxide and it is finally isolated by conventional processes described in the examples.

The monoalkylation and dialkylation reactions are performed either through the action of an alkyl halide, by the action of an aldehyde and formic acid, called reducing alkylation.

In the first case (reactions b and d), the solvents used are inert with respect to alkyl halides, e.g. toluene and acetonitrile. In general terms, 0.5 to 1.5 mol of halide dissolved in 2 to 3 liters of the selected solvent is used for 1 mol of product to undergo alkylation. The preferred ratio is 0.85 to 1.20 mol of alkyl bromide or iodide per mol of reacted product. Optionally a base is added and this can be of a mineral nature, such as anhydrous sodium carbonate, or an organic nature, such as triethylamine, in order to assist the reaction. The appropriate temperatures and times are 40° to 114° C. for 2 to 5 hours. The alkyl products are then separated and purified by conventional methods described in the examples.

In the second case of reducing alkylations (reactions e and e') the reaction consist of initially reacting the aforementioned aldehydes R$_4$-CHO with the product to undergo alkylation. The non-isolated intermediates are then reduced with pure formic acid, the first part of the reaction being carried out at a temperature between 20° and 50° C. and the second part at between 60° and 100° C. for between 1 and 5 hours.

In general terms, the monoalkylations or dialkylations performed by said method require for 1 mol of product to be alkylated, 1.2 to 3.5 mols of pure aldehyde or in 30 to 40% by weight aqueous solution for the formaldehyde and 2 to 5 mols of pure formic acid, the reducing actions of the formic acid being obtained by heating the mixture for 1 to 2 hours at 90° to 100° C.

The aforementioned acylation reactions (c) are performed either in an anhydrous single-phase medium, such as toluene and in the presence of an organic base such as triethylamine, or in a two-phase medium, such as in a water-1,2-dichloroethane mixture in the presence of sodium hydroxide. In both cases, the acid chloride is used in a stoichiometric ratio or in a smaller quantity than the aminoalcohol used.

Generally, for one molecule of aminoalcohol in 2 to 10 liters of solvent, the mineral or organic base is introduced cold, followed by the acid chloride at a rate of 0.5 to 1 mol. The reaction is carried out by stirring the mixture for 1 to 5 hours at a temperature between 0° to 30° C. and preferably for 1 to 2 hours at between 10° and 20° C., before treating the same for isolating the product.

On p 2, lines 37 to 42 of British patent No. 1,434,826 appears a very general formula for alcohols covering the compounds according to the invention. However, no detailed preparation process or precise example is given. These alcohols are not presented as having a pharmacological activity. They are in fact novel compounds which have never been prepared and the formula given on paper is only simple conjecture.

the invention is illustrated in a non-limitative manner by the following examples, in which the methods used are known. However, certain definitions are required.

During the extraction processes, the organic phases containing the expected products are washed by extractions with water or a sodium chloride saturated solutions up to neutrality of said washing liquors. Their residual water is eliminated prior to evaporating the solvent by spending several hours on a dehydrating agent, such as anhydrous sodium sulphate. Evaporation of the solvents takes place in vacuo and on a water bath, whose temperature is adapted to the boiling point of the solvent to be eliminated. In the case of products purified by crystallization, the solvents used for this purpose are given in the text or following the vapour of the boiling point of the product obtained. The residual solvents are removed from the products isolated in solid, crystalline or amorphous form by heating in vacuo to constant weight. The hydrochlorides of the products are systematically prepared according to the operating procedure described in example 1.

Furthermore, the purity, identity and physicochemical characteristics of the products according to the invention are determined by the methods briefly defined hereinafter.

The melting points are determined by the capillary tube method using a "Mettler FP1" apparatus and are not corrected.

The purity is checked by thin layer chromatography: support: silica gel 60 F 254 (supplier Merck), deposits: approximately 100 mcg, elution: rising to 10 cm in the mixtures, A - butanol:acetic acid:water 8:2:2 (v/v/v),
B - methylene chloride:methanol 9:1 (v/v),
C - methylene chloride:methanol 9.5:0.5 (v/v),
D - methylene chloride:acetone 8.2 (v/v),
developing: observation of the plates under ultraviolet light with a wavelength of 254 nm, followed by observation of the plate following atomization of the Dragendorff reagent.

The examples give the migration solvents, used, together with the RF observed. The rotary powers are determined in 2 dm long tubes.

The identity of the products obtained with the structures proposed is checked by their nuclear magnetic resonance spectre of the proton ($^1$H NMR) at 60 MHz. The products are dissolved in deuterochloroform ($CDCl_3$) alone or mixed with dimethyl sulfoxyde, (D-6).

The nature of the signals, their chemical displacements expressed in p.p.m. compared with tetramethylsilane used as the reference, as well as the number of protons which they have are designated for each spectrum. Reference is also made to the so-called "exchangeable" protons following the addition of deuterium oxide.

Throughout the text THF is used for tetrahydrofuran and BMS for borane-dimethyl sulphide.

EXAMPLE 1

1A-($\pm$)
2-methyl-2-amino-3-(3,4-dichlorophenyl)-propanol (JO 1275)

Formula I = $R_1 = CH_3$; $R_2 = R_3 = H$.

625 ml of tetrahydrofuran (THF) and then 24.8 g (0.1 mol) of ($\pm$) 2-(3,4-dichlorobenzyl)-alanine are introduced into a reactor protected against moisture and under a nitrogen atmosphere.

38.0 g (0.5 mol) of borane-dimethyl sulphide (BMS) complex are added dropwise to the suspension obtained over a period 30 minutes and at a temperature of 20° C. Stirring is continued for 15 minutes at ambient temperature. The mixture is then refluxed for 4½ hours. After cooling to 5° C., 75 ml of methanol are gradually introduced without exceeding 20° C. and then in an identical manner 75 ml of N sodium hydroxide solution. The suspension obtained is left overnight, the insoluble being filtered and eliminated. The filtrate evaporated in vacuo and on a water bath gives a white residue, which is taken up by 500 ml of water. The mixture is acidified to pH 1 by adding concentrated hydrochloric acid (d = 1.18).

The solution obtained is extracted twice with 150 ml of ether. The ethereal phases are removed and the acid phase alkalized cold to pH 12 by adding a concentrated sodium hydroxide solution (d = 1.38), followed by sodium chloride saturation.

The alkaline mixture is extracted three times with 200 ml of ether, the combined ethereal phases are washed with a sodium chloride saturated solution and then dried. After evaporating the ether, the aminoalcohol is obtained in the form of a white, amorphous, solid residue.

| Weight: 21.5 g | Yield: 91.8% |
|---|---|
| m.p. = 96° C. | TLC: A - 0.7 |

$^1$H-NMR ($CDCl_3$): 0.95 (s, 3H); 2.25 (s, 3H exchangeable); 2.65 (s, 2H); 3.30 (s, 2H); 6.90–7.40 (m, 3H).

Hydrochloride: 21 g (0.09 mol) of aminoalcohol are dissolved in 220 ml of methylene chloride. Accompanied by stirring and without exceeding 10° C., 90 ml of 3N hydrochloric ether are introduced. After 15 minutes the solvents are evaporated and the residue is again treated in an identical manner with 220 ml of methylene chloride and 60 ml of 3N hydrochloric ether. The crude product obtained after evaporation is purified by crystallization in a mixture of 150 ml of ethanol and 300 ml of ether. The purified, crystallized product is filtered and dried in vacuo at 40° C.

| Weight: 19.6 g | Yield: 80.5% |
|---|---|
| m.p. = 171° C. | |

Analysis $C_{10}H_{14}Cl_3NO$ Calculated: % C 44.39, H 5.22, Cl 39.31, N 5.18, O 5.91; Found: 44.44, 5.15, 39.20, 5.16, 6.05.

1B-(+)
2-methyl-2-amino-3-(3,4-dichlorophenyl)-propanol (JO 1307)

Formula I: $R_1 = CH_3$; $R_2 = R_3 = H$.

The reduction according to the operating procedure described hereinbefore of 23.0 g (92 mmol) of (+) 2-(3,4-dichlorobenzyl)alanine makes it possible to obtain the corresponding detrorotary aminoalcohol.

| Weight 20.0 g | Yield = 92.8% |
|---|---|
| m.p. 86° C. | |

$[\alpha]_D^{20} = +1.6°$ (C=5%, methanol).

$^1$H-NMR (CDCl$_3$) identical to the product of example 1A.

Hydrochloride: Yield=92.2%, m.p. 144° C. (acetone).

Analysis C$_{10}$H$_{14}$Cl$_3$No Calculated: % C 44.39, H 5.22, Cl 39.31, N 5.18, O 5.91; Found: 44.33, 5.24, 39.20, 5.10, 5.75.

IC - (−) 2-methyl-2amino-3-(3,4-dichlorophenyl)-propanol

Formula I : R$_1$=CH$_3$; R$_2$=R$_3$=H.

Using an operating procedure identical to that of the previous examples, the leverotatory aminoalcohol is obtained by reducing 60.0 g (242 mmol) of (−) 2-(3,4-dichlorobenzyl)-alanine. The crude product is purified by crystallization in an ether-hexane mixture.

| Weight: 55.6 g | Yield = 98.1% |
|---|---|
| m.p. 85° C. | TLC: A; 0.7 |

$[\alpha]_D^{20} = 1.8°$ (C=5%, methanol).

$^1$H-NMR (CDCl$_3$) identical to 1A and 1B. cl EXAMPLE 2

(±) 2-isopropyl-2-amino-3 (3,4-dichlorophenyl)-propanol (JO 1579)

Formula I - R$_1$=CH(CH$_3$)$_2$; R$_2$=R$_3$=H.

The product is prepared according to the operating procedure of example 1A from 67.2 g (0.243 mol) of (±) 2-isopropyl-2-(3,4-dichlorobenzyl)-glycine.

After the evaporation of the extraction solvent, the product is obtained in the form of an amorphous white solid.

| Weight: 39.0 g | Yield = 61.2% |
|---|---|
| m.p. = 85° C. | TLC: A: 0.7. |

$^1$H-NMR (CDCl$_3$):0.85 (d, 3H); 1.00 (d,3H; 1.35–2.00 (m,4H, 3H exchangeable); 2.65 (s, 2H); 6.90–7.45 (m, 3H).

Hydrochloride: Yield 83.5%, m.p. 176.5° C. (ethyl acetate).

Analysis C$_{12}$H$_{18}$Cl$_3$NO, 0.75 H$_2$O; Calculated: % C 46.17, H 6.25, Cl 34.08, N 4.48, O 8.96; Found: 46.16, 6.15, 34.34, 4.43, 8.84.

EXAMPLE 3

(±) 2-pentyl-2-amino-3 (3,4-dichlorophenyl)-propanol (JO 1562)

Formula I - R$_1$=(CH$_2$)$_4$-CH$_3$; R$_2$=R$_3$=H.

The product is prepared according to the operating procedure of example 1A from 60.0 g (0.197 mol) of (±) 2-pentyl-2-(3,4-dichlorobenzyl)-glycine.

| Weight: 43.0 g | Yield = 75.2% |
|---|---|

| m.p. = 36° C. (hexane) | TLC: A; 0.85. |
|---|---|

$^1$H-NMR (CDCl$_3$): 0.95 (t, 3H); 1.35 (s, 8H); 2.90 (m, 3H, exchangeable); 2.75 (s, 2H); 3.35 (s, 2H); 7.00–7.50 (m, 3H).

Hydrochloride: Yield 82.1%, m.p. 155° C. (acetone).

Analysis C$_{14}$H$_{22}$Cl$_3$NO: Calculated% C 51.47, H 6.79, Cl 32.56, N 4.28, O 4.90; Found: 51.33, 6.73, 32.42, 4.20, 4.89.

EXAMPLE 4

4A - stage 1: (±) N-formyl-2-(3,4-dichlorobenzyl)-alanine

Intermediate IV R$_1$=CH$_3$; R$_4$=H.

49.6 g (0.2 mol) of (±) 2-(3,4-dichlorbenzyl)-alanine are dissolved in 80.0 ml of pure formic acid (d=1.22) in an apparatus protected from humidity. Accompanied by stirring, the mixture is heated to 60° C. and the thus obtained solution is kept at this temperature for 15 minutes, after which 63.0 ml of pure acetic anhydride are introduced over a period of 40 minutes and at a temperature between 58° and 62° C.

After 15 minutes, 13.0 ml of water are slowly introduced and the solution progressively cooled. At around 40° C. crystallization starts and is completed with stirring at 5° C. for 2 hours.

The product is filtered, washed with ice water up to neutrality of the washing waters, then dried in vacuo at 80° C. to constant weight.

| Weight: 32.6 g | Yield = 59.0% |
|---|---|

$^1$H-NMR (DMSO-CDCl$_3$) 1.45 (s, 3H); 3.25 (s,2H); 6.95–7.50 (m, 3H); 7.90 (s, 1H exchangeable); 8.00 (d, 1H); 10.65 (s wide, 1H exchangeable).

Stage 2: (±) 2-methyl-2-methylamino-3-(3,4-dichlorophenyl)-propanol (JO 1276)

Formula I: R$_1$=R$_2$=CH$_3$; R$_3$=H.

Under a nitrogen atmosphere and protected from humidity, 21.3 g (77.1 mmol) of the product obtained in stage 1 are dissolved in 400 ml of THF.

29.2 g (385 mmol) of the BMS complex are introduced at 20° C. and for 30 minutes. The mixture is then refluxed for 4½ hours and then cooled to 5° C.

Successively and dropwise 65.0 ml of methanol, then 65 mol of sodium hydroxide solution are introduced without exceeding 20° C. The insoluble is filtered and eliminated, the residue obtained after concentration of the filtrate being dissolved in 350 ml of normal hydrochloric acid.

The solution is extracted three times with 125 ml of ether and then alkalized at pH 12 using a sodium chloride saturated concentrated soda solution.

The alkaline mixture is extracted three times using 200 ml of methylene chloride. The combined organic phases are treated in a conventional manner and after evaporation the product is obtained in the form of an amorphous, white solid.

| Weight: 13.4 g | Yield = 70.1% |
|---|---|

|                |                |
| -------------- | -------------- |
| m.p. = 123° C. | TLC: A; 0.5.   |

¹H-NMR (DMSO-CDCl₃) 0.95 (s, 3H); 2.35 (s, 4H whereof 1H exchangeable); 2.65 (s, 3H whereof 1H exchangeable); 3.25 (s, 2H); 6.95–7.50 (m, 3H).

Hydrochloride: Yield=73.0%, m.p. 226° C. (ethanol). Analysis $C_{11}H_{16}Cl_3NO$; Calculated: % C 46.42, H 5.67, Cl 37.37 N 4.92 O 5.62; Found: 46.58, 5.67, 37.30, 4.85, 5.79.

4B - stage 1: (+)
N-formyl-2-(3,4-dichlorobenzyl)-alanine

Intermediate IV $R_1=CH_3$; $R_4=H$.

The product is prepared from (+) 2-(3,4-dichlorobenzyl)-alanine according to the operating procedure of example 4A - stage 1 with a yield of 70.6%.

¹H-NMR (DMSO-CDCl₃) 1.45 (s, 3H); 3.30 (9, 2H); 7.05–7.65 (m, 4H whereof 1 exchangeable); 8.10 (d, 1H); 10.35 (s wide, 1H exchangeable).

Stage 2: (+)
2-methyl-2-methylamino-3-(3,4-dichlorophenyl)-propanol (JO 1308)

Formula I $R_1=R_2=CH_3$, $R_3=H$.

19.0 g of the product obtained in the previous stage (69 mmol) are reduced by the BMS complex according to the operating procedure of stage 2 of example 4-A. The crude product is purified by crystallization in methylene chloride.

|                     |                          |
| ------------------- | ------------------------ |
| Weight: 10.7 g      | Yield = 62.5%            |
| m.p. = 113° C.      | TLC: A; 0.5              |
| $[\alpha]^{D20}$ =  | +(C = 5%, methanol).     |

¹H-NMR (DMSO-CDCl₃) identical to the racemic product of example 4A.

EXAMPLE 5

Stage 1: (±)
N-formyl-2-pentyl-2-(3,4-dichlorobenzyl)-glycine

Intermediate IV $R_1=(CH_2)_4CH_3$; $R_4=H$.

The product is prepared according to example 4 - stage 1 from 50.0 g (0.164 mol) of (±) 2-pentyl-2-(3,4-dichlorobenzyl)-glycine.

|                    |               |
| ------------------ | ------------- |
| Weight: 47.8 g     | Yield = 87.7% |
| TLC: A; 0.4        |               |

Stage 2: (±)
2-penthyl-2-methylamino-3-(3,4-dichlorophenyl)-propanol (JO 1563)

Formula I - $R_1=(CH_2)_4-CH_3$; $R_2=CH_3$, $R_3=H$.

In accordance with the method of example 4 - stage 2, the product is obtained by reducing 47.4 g (0.143 mol) of the derivative obtained in the preceding stage 1.

|                    |               |
| ------------------ | ------------- |
| Weight: 33.0 g     | Yield = 75.8% |
| TLC: A; 0.75.      |               |

¹H-NMR (DMSO-CDCl₃) 0.95 (t, 3H); 1.30 (s, 8H); 1.85 (s, 2H, exchangeable); 2.35 (s, 3H); 2.65 (s, 2H); 3.25 (5s, 2H); 6.95–7.50 (m, 3H).

Hydrochloride: Yield=53.2%, m.p. 151° C. (ethyl acetate). Analysis $C_{15}H_{24}Cl_3NO$; Calculated: % C 52.87, H 7.10, Cl 31.22, N 4.11, O 4.70; Found: 52.81, 7.14, 31.06, 4.08, 4.61.

EXAMPLE 6

The reduction of the (±), (+) and (−) N-acetyl-2-(3,4-dichlorobenzyl)-alanine by the BMS complex makes it possible to obtain the corresponding aminoalcohols of example 6A, 6B and 6C using the operating procedure described in stage 2 of example 4A and B.

6A - (±)
2-methyl-2-ethylamino-3-(3,4-dichlorophenyl)-propanol (JO 1277)

Formula I: $R_1=CH_3$; $R_2=H$; $R_3=C_2H_5$
Yield=71.7% TLC: A; 0.6.
m.p.=110° C. (methylene chloride).

¹H-NMR (DMSO-CDCl₃) 0.85–1.20 (m, 6H); 2.40–2.85 (m, 4H); 2.90–3.15 (m, 2H exchangeable); 3.25 (s, 2H); 6.90–7.40 (m, 3H)

Hydrochloride: Yield=74.9%, m.p.=245° C. (ethanol) Analysis $C_{12}H_{18}Cl_3NO$; Calculated: % C 48.26, H 6.08, Cl 35.62, N 4.69, O 5.36; Found: 48.32, 6.01, 35.63, 4.58, 5.45.

6B - (+)
2-methyl-2-ethylamino-3-(3,4-dichlorophenyl)-propanol (JO 1295)

Formula I: $R_1=CH_3$; $R_2=H$; $R_3=C_2H_5$
Yield=55.6% TLC=A; 0.6,
m.p.=105° C. (ether).

¹H-NMR (DMSO-CDCl₃) identical to the product of example 6A.

Hydrochloride: Yield=82.2%, m.p. 268° C. (methanol), $[\alpha]_D^{20}=+4.2°$ (C=1%, water).

Analysis $C_{12}H_{18}Cl_3NO$; Calculated: % C 48.26, H 6.08, Cl 35.62, N 4.69, O 5.36; Found: 48.22, 6.02, 35.58, 4.63, 5.19.

6C - (−)
2-methyl-2-ethylamino-3-(3,4-dichlorophenyl)-propanol (JO 1296)

Formula I: $R_1=CH_3$; $R_2=H$; $R_3=C_2H_5$.
Yield=67.9%; TOC: A;06.
m.p.=107° C. (ether).

¹H-NMR (DMSO-CDCl₃) identical to the product of example 6A.

Hydrochloride: Yield=75.6%, m.p. 269° C. (methanol-ether).

$[\alpha]_D^{20}=-5°$ (C=1%, water).

Analysis $C_{12}H_{18}Cl_1NO$; Calculated: % C 48.26, H 6.08, Cl 35.62, N 4.69, O 5.36; Found: 48.16, 6.13, 35.75, 4.53, 5.31.

EXAMPLE 7

(±)
2-methyl-2-allylamino-3-(3,4-dichlorophenyl)-propanol (JP 1453)

Formula I: $R_1=CH_3$, $R_2=H$, $R_3=CH_2-CH=CH_2$.

30.0 g (128 mmol) of (±) 2-methyl-2-amino-3-(3,4-dichlorophenyl)-propanol (JO 1275 - ex. 1A) and 14.0 g (116 mmol) of allyl bromide are suspended in 300 ml of acetonitrile in a reactor protected from moisture and accompanied by stirring. The mixture is kept for 1 hour at ambient temperature and then heated for 2 hours at 30° to 50° C.

After cooling, the insoluble is filtered and suspended in 2 liters of demineralized water, alkanized with caustic soda solution and the mixture is extracted 3 times using 750 ml of ether. The combined ethereal phases are treated in a conventional manner. After evaporating the ether, the residue of 13.8 g is crystallized in 1 liter of hexane. The product is filtered and then dried in vacuo.

| Weight: 11.2 g | Yield = 31.9 g |
|---|---|
| m.p. = 106° C. | TLC: B, 0.4 |

$^1$H-NMR (CDCl$_3$) 1.00 (s, 3H); 1.90 (s, wide, 2H exchangeable), 2.65 (s, 2H); 3.10–3.35 (m, 4H); 5.15 (t, 2H); 5.60–6.25 (m, 1H); 6.90–7.45 (m, 3H).

Hydrochloride: Yield = 94.7%, m.p. = 230° C. (ethanol-ether)

Analysis: C$_{13}$H$_{18}$Cl$_3$NO; Calculated: % C 50.26, H 5.84, Cl 34.24, N 4.51, O 5.15; Found: 50.22, 5.75, 34.33, 4.44, 5.00.

EXAMPLE 8

8A - (±)
N-cyclopropanecarboxy-2-methyl-2-amino-3-(3,4-dichlorophenyl)-propanol Formula I: R$_1$=CH$_3$; R$_2$=H;

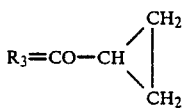

0.57 g (14.2 mmol) of sodium hydroxide in the form of pellets dissolved in 25 ml of water are added to a solution of 5.0 g (21.3 mmol) of aminoalcohol according to example 1A (JO 1275) in 100 ml of 1,2-dichloroethane.

The mixture is vigorously stirred and cooled to 5° C., followed by the dropwise addition in 30 minutes of 1.48 g (14.2 mmol) of cyclopropanecarboxylic acid chloride at a temperature below 10° C. Stirring is maintained for 1 hour at 5° to 10° C., then the organic phase is separated and extracted by 20 ml of normal hydrochloric acid and then treated in the conventional manner.

After separating the solvent, the product is obtained in the form of a yellow viscous oil.

| Weight: 4.3 g | Yield = 66.6% |
|---|---|
| TLC: B: 0.65–0.75 | |

$^1$H-NMR (CDCl$_3$) 0.55–1.65 (m, 7H), 3.05 (q, 2H); 3.55–3.85 (m, 3H), 5.10 (q, 1H exchangeable); 5.55 (s wide, 14); 6.90–7.45 (m, 3H).

8B - (±)
2-methyl-2-cyclopropanemethylamino-3-(3,4-dichlorophenyl)-propanol (JO 1454).

Formula: R$_1$=CH$_3$; R$_2$=H.

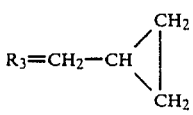

4.2 g (13.9 mmol) of amino alcohol of example 8A are dissolved in 60 ml of THF in a reactor protected from humidity. Under a nitrogen atmosphere, introduction takes place in the conventional manner of 3.16 g (41.7 mmol) of BMS, followed by the refluxing of the mixture for 4½ hours. After cooling, successively 6.0 ml of methanol and then 6.0 ml of N sodium hydroxide solution are added.

After filtering the insoluble, the residue obtained by concentrating the filtrate is taken up in 100 ml of 2N hydrochloric acid. The acid suspension is extracted twice with 50 ml of ether, then alkalized to pH 12 with caustic soda solution and then again extracted with ether. The ethereal phases are combined and treated in the conventional manner. Following evaporation, the aminoalcohol is obtained in the form of a viscous oil.

| Weight: 2.9 g | Yield = 72.4% |
|---|---|
| TLC: B, 0.25–0.4 | |

$^1$H-NMR (CDCl$_3$) 0.05–1.25 (m, 7H); 2.05 (s wide; 2H exchangeable); 2.45 (d, 2H); 2.65 (s, 2H); 3.20 (s, 2H); 6.90–7.45 (m, 3H).

Hydrochloride:

| Yield = 86.3% | m.p. = 237° C. |
|---|---|
| (ethanol-ether) | |

Analysis: C$_{14}$H$_{20}$Cl$_3$NO; Calculated: % C 51.79, H 6.21, Cl 32.76, N 4.31, O 4.93; Found: 51.87, 6.10, 32.69, 4.27, 4.83.

EXAMPLE 9

9A - (±)
N-pivalyl-2-methyl-2-amino-3-(3,4-dichlorophenyl)-propanol

Formula I: R$_1$=CH$_3$; R$_2$=H; R$_3$=—CO—C(CH$_3$)$_3$.

3.7 g (36 mmol) of triethylamine are added to a suspension of 5.0 g (21.3 mmol) of aminoalcohol of example 1A (JO 1275) in 30.0 ml of toluene.

At 4° C. and accompanied by stirring, a solution of 2.53 g (21 mmol) of pivaloyl chloride in 30.0 ml of toluene are added within 1 hour. Stirring is continued for 1 hour following introduction and the solution is then extracted twice with 25 ml of N hydrochloric acid. The toluene phase is extracted again using twice 25 ml of saturated sodium bicarbonate solution and is then treated in the usual way. After eliminating the toluene, the product of obtained in the form of a pale yellow viscous oil.

| Weight: 6.0 g | Yield = 89.7% |
|---|---|
| TLC: B, 0.6–0.7 | |

$^1$H-NMR (CDCl$_3$) 0.90–1.25 (m, 12H); 2.95 (q, 2H); 3.60 (d, 2H); 4.90 (t, 1H exchangeable); 5.40 (s wide, 1H); 6.85–7.40 (m, 3H).

9B - (±)
2-methyl-2-(2,2-dimethyl)propylamino-3-(3,4-dichlorophenyl)-propanol (JO 1455)

Formula I: R$_1$=CH$_3$; R$_2$=H; R$_3$=—CH$_2$—C(CH$_3$)$_3$

According to the operating procedure described in example 8B, 5.4 g (17 mmol) of the previously obtained amide are reduced by 2.6 g (34 mmol) of BMS complex.

| Weight: 4.5 g | Yield = 87.0% |
|---|---|
| m.p. = 91° C. (hexane) | TLC: B, 0.45–0.55 |

$^1$H-NMR (CDCl$_3$) 0.95 (s, 12H); 1.30–2.05 (m wide, 2H exchangeable); 2.25 (s, 2H); 2.65 (s, 2H); 3.25 (s, 2H); 6.90–7.45 (m, 3H).

Hydrochloride: Yield=71.5% m.p.=225° C. (methanol-ether)

Analysis: C$_{15}$H$_{24}$Cl$_3$NO; Calculated: % C. 52.87, H 7.10, Cl 31.22, N 4.11, O 4.69; Found: 53.02, 6.98, 31.15, 4.09, 4.57.

EXAMPLE 10

10A - (±) N-phenylacetyl-2-methyl-2-amino-3-(3,4-dichlorophenyl)-propanol

Formula I: R$_1$=CH$_3$; R$_2$=H; R$_3$=CO—CH$_2$—C$_6$H$_5$

The product is prepared according to the operating procedure described in example 8A by reaction between 2.2 g (14.2 mmol) of phenylacetic acid chloride and 5.0 g (21.3 mmol) of aminoalcohol obtained in example 1A (JO 1275).

| Weight: 4.9 g | Yield = 65.3% |
|---|---|
| TLC: C, 0.80 | |

$^1$H-NMR (CDCl$_3$) 1.05 (s, 3H); 2.90 (q, 2H); 3.55 (d, 2H); 4.70 (s, 2H); 4.90 (s wide, 1H exchangeable); 5.45 (s wide, 1H); 6.70–7.50 (m, 8H).

10B - (±) 2-methyl-2-(2-phenyl)-ethylamino-3-(3,4-dichlorophenyl)-propanol (JO 1456)

Formula I: R$_1$=CH$_3$; R$_2$=H; R$_3$=—CH$_2$—CH$_2$—C$_6$H$_5$.

Obtained according to the operating procedure of example 8B by reducing 4.8 g (13.6 mmol) of the previously described aminoalcohol with 3.1 g (40.8 mmol) of BMS complex.

| Weight: 2.9 g | Yield = 63.0% |
|---|---|
| m.p. = 113° C. (hexane) | TLC: B, 0.6–0.7 |

$^1$H-NMR (CDCl$_3$) 0.90 (s, 3H); 1.3–2.2 (m wide, 2H exchangeable); 3.55 (s, 2H); 3.75 (s, 4H); 3.15 (s, 2H); 6.75–7.35 (m, 8H).

Hydrochloride: Yield=84.0%, m.p.=235° C. (ethyl acetate).

Analysis: C$_{18}$H$_{22}$Cl$_3$NO; Calculated: % C 57.29, H 5.92, Cl 28.38, N 3.74, O 4.27; Found: 57.65, 5.84, 28.30, 3.68, 4.22.

EXAMPLE 11

(±) 2-methyl-2-(N-methyl, N-ethyl)-amino-3-(3,4-dichlorophenyl)-propanol (JO 1291)

Formula I: R$_1$=CH$_3$; R$_2$=CH$_3$; R$_3$=C$_2$H$_5$.

On a water bath at approximately 50° C., 20.0 g (76.3 mmol) of aminoalcohol of example 6A (JO 1277) are intimately mixed with 17.6 ml of 30% formaldehyde solution (wt/v). The thus obtained paste is cooled to 15° C. and 12.9 ml of pure formic acid (d=1.22) are gradually added, the mixture then becoming less viscous and a solution is obtained which is heated for 1 hour at 30° to 100° C.

Following cooling, 100 ml of ice water are added, the solution is acidified to pH 1 using concentrated hydrochloric acid and then extracted three times with 50 ml of ether.

The acid phase is alkalized with a concentrated sodium hydroxide solution and then extracted three times with 75 ml of ether. The ethereal phases are treated in the conventional manner and the oily residue obtained after evaporating the ether is crystallized in 150 ml of hexane. The white crystalline product is filtered and dried.

| Weight: 19.45 g | Yield = 92.3% |
|---|---|
| m.p. = 55° C. | |

$^1$H-NMR (CDCl$_3$) 0.95 (s, 3H); 1.10 (t, 3H); 2.30 (s, 3H); 2.55 (d, 2H); 2.65 (s, 2H); 3.00 (s wide, 1H exchangeable); 3.25 (d, 2H); 6.90–7.45 (m, 3H).

Hydrochloride: Yield=64.4%, m.p.=192° C. (ethanol).

Analysis: C$_{13}$H$_{20}$Cl$_3$NO; Calculated: % C 49.94, H 6.45, Cl 34.02, N 4.48, O 5.12, Found: 49.83, 6.35, 33.93, 4.38, 5.21.

EXAMPLE 12

(±) 2-methyl-2-[N-methyl, N-(2-phenyl)-ethyl]-amino-3-(3,4-dichlorophenyl)-propanol (JO 1457)

Formula I: R$_1$=CH$_3$; R$_2$=CH$_3$; R$_3$=CH$_2$—CH$_2$—C$_6$H$_5$.

The product is prepared in accordance with the operating procedure of the preceding example starting with 8.9 g (26.3 mmol) of aminoalcohol prepared according to example 10B (JO 1456). The product is in the form of a viscous oil.

| Weight: 8.8 g | Yield = 95.0% |
|---|---|
| TLC = C, 0.55 | |

$^1$H-NMR (CDCl$_3$) 0.85 (s, 3H); 2.20 (s wide, 1H exchangeable); 2.25 (s, 3H); 2.40–2.75 (m, 6H); 3.10 (d, 2H); 6.85–7.35 (m, 8H).

Hydrochloride: Yield=65.3%; m.p.=212° C. (ethanol-ether).

Analysis: C$_{19}$H$_{24}$Cl$_3$NO; Calculated: % C 58.70 H 6.22, Cl 27.36, N 3.60, O 4.11; Found: 58,62, 6.17, 27.31, 3.57, 4.03.

EXAMPLE 13

(±) 21-methyl-2-(N-methyl, N-allyl)-amino-3-(3,4-dichlorophenyl)-propanol (JO 1581)

Formula I R$_1$=(CH$_3$); R$_2$=R$_3$=CH$_2$—CH=CH$_2$.

The product is prepared according to the operating procedure of example 11 from 3.8 g (13.8 mmol) of aminoalcohol obtained in example 7. The product is obtained in the form of a pale yellow viscous oil.

| Weight: 3.8 g | Yield = 95.5% |
|---|---|
| TLC: B, 0.60 | |

$^1$H-NMR (CDCl$_3$) 0.95 (s, 3H); 2.25 (s, 3H); 2.70 (s, 2H); 2.90 (s, 1H exchangeable); 3.15 (d, 2H); 3.25 (d, 2H); 5.25 (d, 2H); 5.55–5.95 (m, 1H); (6.95–7.45 (m, 3H).

Hydrochloride: Yield=86.5%, mp. 190° C. (ethyl acetate).

Analysis: C$_{14}$H$_{20}$Cl$_3$NO; Calculated: % C 51.79, H 6.21, Cl 32.76, N 4.31, O 4.93; Found: 51.73, 6.21, 32.68, 4.26, 5.05.

The products of examples 14A, 14B and 14C are respectively obtained from the aminoalcohols of examples 1A (JO 1275), 1B (JO 1307) and 1C by reacting with formaldehyde and formic acid. This also applies with regards to the products of examples 15 and 16, which are respectively prepared from the aminoalcohols of examples 2 and 3.

Operating Procedure

To 0.1 mol of aminoalcohol are added 24.6 ml of 37% formaldehyde solution (wt/v), i.e. 9.0 g (0.3 mol). The reagents are vigorously mixed, whilst making tepid if necessary, in order to obtain a homogeneous gum, to which is gradually added and, whilst cooling if necessary, 18.9 ml (0.5 mol) of 99 to 100% formic acid (d=122). The viscous mixture is placed for 1½ hours on the boiling water bath, then cooled to 20° C. and then 125 ml of water are added thereto.

The solution is acidified to pH 1 using concentrated hydrochloric acid and extracted three times with 50 ml of ether. The ethereal phases are removed and the acid phase alkalized to pH 12 using a concentrated sodium hydroxyde solution, followed by again extracting three times with 75 ml of ether. The combined ethereal phases are treated in the conventional manner.

EXAMPLE 14

14A-(±)
2-methyl-2-dimethylamino-3-(3,4-dichlorophenyl)-propanol (JO 1017)

Formula I: R$_1$=R$_2$=R$_3$=CH$_3$ white crystals.

| Yield = 79.2% | m.p. = 88° C. (hexane) |
|---|---|
| TLC: A, 0.4–0.5 | |

$^1$H-NMR (CDCl$_3$) 0.90 (s, 3H); 2.30 (s, 6H); 2.65 (s, 2H); 3.10 (s wide, 1H exchangeable); 3.20 (s, 2H); 6.95–7.45 (m, 3H)

Hydrochloride: Yield=84.0%, m.p.=177° C. (ethanol).

Analysis: C$_{12}$H$_{18}$Cl$_3$NO; Calculated: % C 48.26, H 6.07, Cl 35.62, N 4.69, O. 5.36; Found: 48.35, 6.04, 35.47, 4.70, 5.43.

14B-(−)
2-methyl-2-dimethylamino-3-(3,4-dichlorophenyl)-propanol (JO 1239

Formula I: R$_1$=R$_2$=R$_3$=CH$_3$.
Oil: Yield=53.1%, TLC: A, 0.4–0.5
[α]$_D^{20}$ = −6.5° (c=1%, ethanol).
$^1$H-NMR (CDCl$_3$) identical to the product of example 14A.

Hydrochloride: Yield 79.2%, m.p.=192° C. (ethanol).

Analysis: C$_{12}$H$_{18}$Cl$_3$NO; Calculated: % C 48.26, H 6.07, Cl 35.62, N 4.69, O 5.36; Found: 48.21, 6.09, 35.55, 4.63, 5.39.

14C- (+)
2-methyl-2-dimethylamino-3-(3,4-dichlorphenyl)-propanol (JO 1240

Formula I: R$_1$=R$_2$=R$_3$=CH$_3$.
Oil-Yield=66.5%; TLC: A, 0.4–0.5
[α]$_D^{20}$ +6.2° (C=2%, ethanol).
$^1$H-NMR (CDCl$_3$) identical to the products of examples 14A and B.

Hydrochloride: Yield=79.7%, m.p.=193° C. (ethanol).

Analysis: C$_{12}$H$_{18}$Cl$_3$NO; Calculated: % C 48.26, H 6.07, Cl 35.62, N 4.69, O 5.36; Found: 48.16, 6.12, 35.61, 4.57, 5.45.

EXAMPLE 15

(±)
2-isopropyl-2-dimethylamino-3-(3,4-dichlorophenyl)-propanol (JO 1580)

Formula I-R$_1$=CH(CH$_3$)$_2$; R$_2$=R$_3$=CH$_3$.
Oil: Yield=96.6%, TLC: A, 0.65.
$^1$H-NMR (CDCl$_3$) 0.80–1.20 (m, 6H); 1.65–2.20 (m, 1H); 2.40 (s, 6H); 2.75 (s, 2H); 3.20 (s, 1H exchangeable); 3.45 (s, 2H); 7.00–7.45 (m, 3H).

Hydrochloride: Yield=92.9%, m.p.=178° C. (acetone).

Analysis: C$_{14}$H$_{22}$Cl$_3$NO; Calculated: % C 51.47, H 6.79, Cl 32.56, N 4.29, O 4.89; Found: 51.56, 6.59, 32.53, 4.26, 4.98.

EXAMPLE 16

(±)
2-pentyl-2-dimethylamino-3-(3,4-dichlorophenyl)-propanol (JO 1564)

Formula I-R$_1$=(CH$_2$)$_4$CH$_3$; R$_2$=R$_3$=CH$_3$.
Oil: Yield=92.5%; TLC: A, 0.65.
$^1$H-NMR (CDCl$_3$): 0.80 (t, 3H); 1.30 (s, 8H); 2.35 (s, 6H); 2.65 (s, 2H); 3.25 (s, 3H whereof 1H exchangeable); 6.85–7.35 (m, 3H).

Hydrochloride: Yield=92.7% m.p.=160° C. (ethyl acetate).

Analysis: C$_{16}$H$_{26}$Cl$_3$NO; Calculated: % C 54.17, H 7.38, Cl 29.98, N 3.95, O 4.51; Found: 54.15, 7.26, 29.82, 3.88, 4.60.

EXAMPLE 17

(±)
2-methyl-2-(1-piperidyl-3-(3,4-dichlorophenyl)-propanol JO 1467)

Formula I: R$_1$=CH$_3$; NR$_2$—NR$_3$=piperidyl.

5 g (21.3 mmol) of the aminoalcohol obtained in example 1A and 5.14 g (22.3 mmol) of 1,5-dibromopentane are dissolved in 40 ml of toluene in a reactor protected from humidity.

The solution is refluxed whilst stirring for 1 hour and then cooled to ambient temperature. 4.58 g (43.2 mmol) of sodium carbonate are then added and the suspension obtained again refluxed for 20 hours. After cooling, 100 ml of 2N hydrochloric acid are slowly added, the insoluble filtered and washed with toluene.

The filtrate is eliminated and the insoluble taken up with 500 ml of water. The suspension obtained is alkalized in pH 12 by adding 10N sodium hydroxyde solution. The mixture is extracted three times using 250 ml of ether. The combined ethereal phases are treated in the conventional way. After evaporating, the product is obtained in the form of a white, amorphous solid.

| Weight: 2.2 g | Yield = 34.2% |
|---|---|
| m.p. = 94° C. | TLC: A, 0.6 |

$^1$H-NMR (CDCl$_3$): 0.95 (s, 3H); 1.55 (s wide, 6H); 2.50–2.75 (m, 6H); 2.90 (s, H exchangeable); 3.30 (q, 2H); 6.90–7.45 (m, 3H).

Analysis: C$_{15}$H$_{21}$Cl$_2$NO; Calculated: % C 59.61, H 7.00, Cl 23.46, N 4.63, O 5.29; Found: 59.42, 6.99, 23.58, 4.74, 5.30.

EXAMPLE 18

(±)
2-methyl-2-(4-morpholinyl)-3-(3,4l-dichlorophenyl)-propanol (JO 1565)

Formula I-R$_1$=CH$_3$; NR$_2$-R$_3$=morpholine.

23.4 g (0.1 mol) of aminoalcohol obtained in example 1A are dissolved in 300 ml of dimethylformamide in a reactor protected against humidity.

Accompanied by stirring, 15.7 g (0.110 mol) of bis-2-chloroethylether and then 18.5 g (0.220 mol) of sodium bicarbonate are added.

Stirring of the suspension is continued for 48 hours at 100° C. The insoluble is filtered and the dimethylformamide eliminated by vacuum distillation. The residue is taken up with ether, the solution then being extracted three times successively with 150, 100 and 100 ml of N HCl solution.

The combined hydrochloric phases are alkalized by adding caustic soda solution of pH 12. The mixture is then extracted with ether. The combined ethereal phases are washed with a saturated sodium chloride solution and then dried on Na$_2$SO$_4$. The ether is eliminated by distillation. Weight of the residue 33.0 g.

This residue is purified by silica column chromatography.

The product is obtained by eluting a methylene chloridemethanol mixture 95:5 (v/v).

| Weight: 14.5 g | Yield = 47.7% |
|---|---|
| TLC: C, 0.75 | |

Hydrochloride: Yield=76.9%, m.p.=232° C. (methanol-ether).

Analysis: C$_{14}$H$_{20}$Cl$_3$NO$_2$; Calculated: % C 49.36, H 5.92, Cl 31.22, N 4.11, O 9.39; Found: 49.38, 5.88, 31.17, 4.03, 9.49.

EXAMPLE 19

(±)
2-methyl-2-(1-(4-methyl)-piperazinyl)-3-(3,4-dichlorphenyl)-propanol (JO 1566)

The product is obtained according to the operating procedure of example 18 starting with 46.8 g (0.200 mol) of the amino-alcohol of example 1A, 42.2 g (0.220 mol) of N-methyl-bis-(2-chloroethyl)-amine hydrochloride and 54 g (0.640 mol) of sodium bicarbonate.

| Weight = 6.2 g | Yield = 9.8% |
|---|---|
| m.p. = 118° C. (ethyl acetate) | TLC: D, 0.45 |

Analysis: C$_{15}$H$_{22}$Cl$_2$N$_2$); Calculated: % C 56.71, H 6.99, Cl 22.35, N 8.83, O5.04; Found: 56.73, 6.82, 22.28, 8.74, 5.20.

$^1$H-NMR (CDCl$_3$): 1.05 (s, 3H); 2.40 (s, 3H); 2.45–3.05 (m, 10H); 3.05–3.65 (m, 3H whereof 1H exchangeable); 6.95–7.50 (m, 3H).

| Weight: 2.2 g | Yield = 34.2% |
|---|---|
| m.p. = 94° C. | TLC: A, 0.6 |

$^1$H-NMR (CDCl$_3$): 0.95 (s, 3H); 1.55 (s wide, 6H); 2.50–2.75 (m, 6H); 2.90 (s, H exchangeable); 3.30 (q, 2H); 6.90–7.45 (m, 3H).

Analysis: C$_{15}$H$_{21}$Cl$_2$NO; Calculated: % C 59.61,H 7.00 Cl 23.46, N 4.63, O 5.29; Found: 59.42, 6.99, 23.58, 4.74, 5.30.

The pharmacological study of the products according to the invention reveals interesting properties and in particular an activity on the central nervous system (S.N.C.), accompanied by analgesic properties. In addition, their toxicity was determined. Details of this research are given below and the results obtained demonstrate the therapeutic activity of these products, as well as their usefulness as medicaments.

The acute toxicity was studied orally on the male mouse. For this purpose, the products were administered in an aqueous solution at a rate of 2 ml/100 g. The animals were then observed for the three hours following administration and then daily for 14 days, when they were killed and autopsied.

The LD$_{50}$ values (lethal does causing the death of 50% of the animals) were calculated according to the method of Reed J. L. and Muench H (Am. J. Hyg. 1939, 27, 493). Their value is generally between 750 and 1200 mg-kg$^{-1}$ and sometimes above the latter figure.

Activity on the S.N.C.

This activity was investigated on mice using the tail hanging test in accordance with the procedure described by Thierry et al. (Behavioral and Neural Biology, 1984, 41, 180–189), which was proposed as a model for the animal for the selection of products active on the S.N.C.

The tests were carried out on batches of 10 male mice for each product and at each dose, the substances to be investigated being administered orally in aqueous solution 1 hour before the test, a control batch only receiving distilled water.

The results of the tests are given in activity percentages compared with the controls.

Analgesic activity

This was investigated and determined on mice using the acetic acid test according to a procedure derived from that of Troster R. (Fed. Proc. 1959, 18, 412).

20 hours prior to the test, the animals were starved of food and drink. This was followed by the oral administration in aqueous solution of the product to be investigated at a rate of 2 ml of solution per 100 g of body weight, which was followed 30 minutes later by an intraperitoneal injection of 0.25 ml of 0.25% acetic acid solution (wt/v) maintained at 37° C. 30 minutes after this injection, the number of abdominal cramps suffered by the animals were counted for a period of 10 minutes.

The animals were considered to be analgesed when the number of cramps suffered was less than half the mean value of the cramps experienced by the controls.

The products were administered at a dose rate of 30 mg-kg$^{-1}$ and the results are given in percentages of analgesed animals. For certain products, several doses were administered and the calculation of their $ED_{50}$ (dose causing analgesia of 50% of the animals) was determined in log probability units.

The results of these two tests are summarized in the following tables I and II.

TABLE II

| Example No. | Laboratory Code | Analgesia: Acetic acid test | |
|---|---|---|---|
| | | Dose: 30 mg/kg | $ED_{50}$ mg/kg |
| 1-A | JO 1275 | −43% | |
| 1-B | JO 1307 | −50% | |
| 4-A | JO 1276 | −86% | 8.5 |
| 4-B | JO 1308 | −88% | |
| 6-A | JO 1277 | −43% | |
| 3-C | JO 1296 | −38% | |
| 11 | JO 1291 | −38% | |
| 14-A | JO 1017 | −86% | 14.0 |
| 14-B | JO 1239 | −86% | 11.0 |
| Noramidopyrine | | | 20 to 23 |

TABLE I

Results of the pharmacological tests

| Example No. | Laboratory Code | S.N.C.: Hanging test | |
|---|---|---|---|
| | | Dose: 32 mg/kg | Dose: 128 mg/kg |
| 1-A | JO 1275 | −78% | −86% |
| 2 | JO 1579 | | −67% |
| 3 | JO 1562 | −73% | |
| 4-A | JO 1276 | −58% | −83% |
| 5 | JO 1563 | −49% | −71% |
| 11 | JO 1291 | −58% | |
| 12 | JO 1457 | −60% | |
| 13 | JO 1581 | | −61% |
| 14-A | JO 1017 | −65% | −85% |
| 14-B | JO 1239 | −74% | −64% |
| 14-C | JO 1240 | −77% | −85% |
| 16 | JO 1564 | | −74% |
| Clomipramine | | −49% | −54% |

As is demonstrated by these results, at doses of 32 and 128 mg-kg$^{-1}$, the products according to the invention have a greater activity on the central nervous system than clomipramine.

The analgesic properties of the products according to the invention are clearly demonstrated at an oral dose of 30 mg-kg$^{-1}$. The calculation of the $ED_{50}$ values demonstrates a superiority of activity compared with the known analgesic Noramidopyrine, taken as the reference substance.

Thus, the products according to the invention have physchotropic and analgesic properties, useful in the form of medicaments for veterinary or human therapeutic purposes.

Inter alia, these preparations are more particularly intended for the treatment of psychopathological and neuropathological disorders, as well as pain syndroms of various etiologies.

They can be used in psychoses and neuroses, e.g. having symptoms such as modifications of the humour, the memory, the psychomotor tonus and certain organic functions.

Moreover, the combination of the psychotropic and analgesic properties of the products make these preparations usable in the treatment of insomnia, headaches, certain migratary or angina pains, as well as in certain nauseous states.

The products according to the invention, as such or in the form of their pharmaceutically acceptable salts are administered in the form of compositions by appropriate routes for the nature and gravity of the ailment to be treated and in forms compatible with the envisaged administration routes.

The relatively low toxicity of these products permits a daily dosage in man of approximately 1 gram of product. Generally the dosage is between 0.010 and 0.500 gram of product daily and this quantity can be divided up into several unit doses.

The pharmaceutical compositions according to the invention consist of 1 to 40% by weight of the active agent constituted by one or more compounds of formula (I) or the salts thereof and 99 to 60% by weight of a pharmaceutical carrier compatible with the physical form of the envisaged composition.

The compositions are prepared by per se known methods and their form is compatible with the administration route. Examples are tablets, dragees, capsules, powders, injectable or drinkable solutions, suspensions, gels and suppositories. Their production is illustrated in a non-limitative manner by the description of the methods for preparing tablets and injectable isotonic solutions with the active constituents according to the invention.

| Tablets | |
|---|---|
| Formulation | |
| Active substance according to example 10A | 5 to 75 mg |
| Polyvinylpyrrolidone | 2 mg |
| Carboxymethyl starch | 8 mg |
| Magnesium stearate | 3 mg |
| Lactose | 60 to 76 mg |
| Monocrystalline cellulose | 122 to 76 mg |
| for one 200 g tablet. | |

Production

Dissolved polyvinylpyrrolidone at a concentration between 0.1 and 1.0% by weight in water or an alcohol with a low molecular weight, such as ethanol or a hydroalcoholic mixture.

Intimately mix the active substance, the lactose, half the crystalline cellulose quantity and the carboxymethyl starch and then humidify this mixture with the previously obtained polyvinylpyrrolidone solution.

Granulate the paste obtained on the oscillating granulator and then dry the granules in the oven or on a fluidized air bed. Calibrate on a screen the dried granules and add magnesium stearate, the remainder of the microcrystalline cellulose and the carboxymethyl starch. Intimately mix and then form into tablets at a rate of 200 mg per tablet.

| Injectable isotonic solution | |
|---|---|
| Formulation | |
| Active substance according to example 1A (in hydrochloride form) | 10 mg |
| Sodium chloride | 9 mg |
| Distilled water (quantity adequate for) | 1.0 ml |

The isotonic solution is placed in ampoules having an appropriate volume and which, after sealing, are sterilized by per se known thermal means or the solution is sterilized by filtration, distributed into ampoules which are then sealed, the operations being performed in a sterile atmosphere. In the latter case, it is preferable to

We claim:
1. An aminoalcohol of the formula

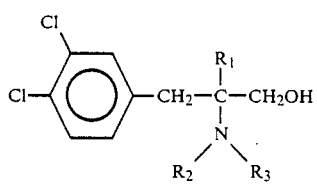

wherein
- $R_1$ is lower alkyl,
- $R_2$ is H or lower alkyl,
- $R_3$ is H, lower alkyl or lower alkenyl and the acid addition salt thereof.

2. The aminoalcohol of claim 1 wherein $R_1$ is methyl.
3. The aminoalcohol of claim 1 wherein $R_2$ is methyl.
4. The aminoalcohol of claim 2 wherein $R_2$ is methyl.
5. The aminoalcohol of claim 1 wherein $R_3$ is methyl.
6. The aminoalcohol of claim 2 wherein $R_3$ is methyl.
7. The aminoalcohol of claim 3 wherein $R_3$ is methyl.
8. The aminoalcohol of claim 1 which is 2-methyl-2-amino-3-(3,4-dichlorophenyl)-propanol or a salt thereof.
9. The aminoalcohol of claim 1 which is 2-pentyl-2-amino-3-(3,4-dichlorophenyl)-propanol or a salt thereof.
10. The aminoalcohol of claim 1 which is 2-methyl-2-methylamino-3-(3,4-dichlorophenyl)-propanol or a salt thereof.
11. The aminoalcohol of claim 1 which is 2-methyl-2-dimethylamino-3-(3,4-dichlorophenyl)-propanol or a salt thereof.
12. Analgesic medicament having an activity on the central nervous system and comprising 1 to 40 percent by weight of an aminoalcohol of formula

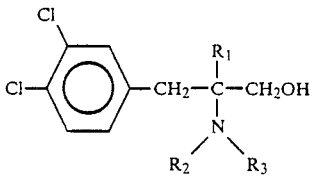

wherein
- $R_1$ is lower alkyl,
- $R_2$ is H or lower alkyl,
- $R_3$ is H, lower alkyl or lower alkenyl and an acid addition salt or salt thereof, and
- 99 to 60 percent by weight of a pharmaceutically acceptable carrier.